(12) United States Patent
Gaines et al.

(10) Patent No.: US 8,798,527 B2
(45) Date of Patent: *Aug. 5, 2014

(54) WIRELESS RELAY MODULE FOR REMOTE MONITORING SYSTEMS

(75) Inventors: Robert B. Gaines, Lake Saint Louis, MO (US); Joel D. Wiesner, St. Peters, MO (US); John Holste, Hamburg, IL (US); Kenneth M. Breitweiser, Brighton, IL (US)

(73) Assignee: Covidien LP, Mansfield, MA (US)

( * ) Notice: Subject to any disclaimer, the term of this patent is extended or adjusted under 35 U.S.C. 154(b) by 191 days.

This patent is subject to a terminal disclaimer.

(21) Appl. No.: 13/241,620

(22) Filed: Sep. 23, 2011

(65) Prior Publication Data
US 2012/0182894 A1 Jul. 19, 2012

Related U.S. Application Data

(63) Continuation-in-part of application No. 13/006,769, filed on Jan. 14, 2011.

(51) Int. Cl.
*H04B 7/15* (2006.01)
*H04B 3/36* (2006.01)
*H04B 7/14* (2006.01)
*G06F 19/00* (2011.01)
*A61B 5/00* (2006.01)
*H04W 88/04* (2009.01)

(52) U.S. Cl.
CPC .......... *A61B 5/0022* (2013.01); *G06F 19/3418* (2013.01); *H04W 88/04* (2013.01)
USPC ...................... 455/11.1; 455/7; 455/9; 455/16

(58) Field of Classification Search
CPC ....................................................... H04B 7/15
USPC .................................... 455/11.1, 15, 16, 41.1
See application file for complete search history.

(56) References Cited

U.S. PATENT DOCUMENTS

| 5,451,839 A | 9/1995 | Rappaport et al. |
| 5,936,539 A | 8/1999 | Fuchs |

(Continued)

FOREIGN PATENT DOCUMENTS

| EP | 2227063 A1 | 9/2010 |
| KR | 10-2008-0016458 A | 2/2008 |

(Continued)

OTHER PUBLICATIONS

PCT International Preliminary Report on Patentability of the ISA; dated Sep. 12, 2013; for PCT Pat. App. No. PCT/US2012/025906; 14 pages.

(Continued)

*Primary Examiner* — Tilahun B Gesesse
(74) *Attorney, Agent, or Firm* — Daly, Crowley, Mofford & Durkee, LLP

(57) ABSTRACT

A wireless relay module for networked communications between a series of medical devices and a remote monitoring device. The relay module communicates with the remote monitoring device over one or more internet-accessible wireless communication networks, and includes a receiver, transmitter for communicating over wireless relay networks, other transmitters for the one or more internet-accessible wireless communications networks; and a controller. The controller determines a status of the one or more internet-accessible wireless communications networks. When the status indicates that at least one of the interne-accessible wireless communications network is available, the appropriate transmitter is selected for the transmitting medical device data over the available internet-accessible wireless communications networks. When internet-accessible wireless communications networks are not accessible, the appropriate wireless relay network transmitter is selected for transmitting the data to another wireless relay module.

29 Claims, 9 Drawing Sheets

(56) References Cited

U.S. PATENT DOCUMENTS

| | | |
|---|---|---|
| 6,221,012 B1 | 4/2001 | Maschke et al. |
| 6,377,162 B1 | 4/2002 | Delestienne et al. |
| 6,377,806 B1 | 4/2002 | Tokuyoshi |
| 6,442,433 B1 | 8/2002 | Linberg |
| 6,519,569 B1 | 2/2003 | White et al. |
| 6,578,002 B1 | 6/2003 | Derzay et al. |
| 6,790,198 B1 | 9/2004 | White et al. |
| 6,839,753 B2 | 1/2005 | Biondi et al. |
| 7,028,182 B1 | 4/2006 | Killcommons |
| 7,050,984 B1 | 5/2006 | Kerpelman et al. |
| 7,082,460 B2 | 7/2006 | Hansen et al. |
| 7,178,149 B2 | 2/2007 | Hansen |
| 7,185,014 B1 | 2/2007 | Hansen |
| 7,236,936 B2 | 6/2007 | White et al. |
| 7,294,105 B1 | 11/2007 | Islam |
| 7,316,648 B2 | 1/2008 | Kelly |
| 7,349,947 B1 | 3/2008 | Slage et al. |
| 7,508,787 B2 | 3/2009 | Doshi et al. |
| 7,529,561 B2 | 5/2009 | Heinonen et al. |
| 7,539,532 B2 | 5/2009 | Tran |
| 7,539,533 B2 | 5/2009 | Tran |
| 7,558,622 B2 | 7/2009 | Tran |
| 7,613,169 B2 | 11/2009 | Vaittinen et al. |
| 7,645,258 B2 | 1/2010 | White et al. |
| 7,707,047 B2 | 4/2010 | Hasan et al. |
| 7,733,224 B2 | 6/2010 | Tran |
| 7,749,164 B2 | 7/2010 | Davis |
| 7,752,058 B2 | 7/2010 | Sasaki et al. |
| 7,827,040 B2 | 11/2010 | Brown |
| 7,873,772 B2 | 1/2011 | Waldhoff et al. |
| 7,937,370 B2 | 5/2011 | Hansen |
| 7,949,404 B2 | 5/2011 | Hill |
| 7,978,062 B2 * | 7/2011 | LaLonde et al. ......... 340/539.11 |
| 8,002,701 B2 | 8/2011 | John et al. |
| RE42,934 E | 11/2011 | Thompson |
| 8,073,008 B2 * | 12/2011 | Mehta et al. .................. 370/468 |
| 8,108,543 B2 | 1/2012 | Hansen |
| 8,125,318 B2 | 2/2012 | Heimbrock et al. |
| 8,326,648 B2 | 12/2012 | Kenedy et al. |
| 8,428,722 B2 | 4/2013 | Verhoef et al. |
| 2002/0178126 A1 | 11/2002 | Beck et al. |
| 2002/0198473 A1 | 12/2002 | Kumar et al. |
| 2004/0155772 A1 | 8/2004 | Medema et al. |
| 2004/0204743 A1 | 10/2004 | McGrath et al. |
| 2005/0010093 A1 | 1/2005 | Ford et al. |
| 2005/0201300 A1 | 9/2005 | Bridgelall |
| 2005/0243988 A1 | 11/2005 | Barclay et al. |
| 2005/0288571 A1 | 12/2005 | Perkins et al. |
| 2006/0154642 A1 | 7/2006 | Scannell, Jr. |
| 2006/0238333 A1 | 10/2006 | Welch et al. |
| 2007/0106126 A1 | 5/2007 | Mannheimer et al. |
| 2007/0156033 A1 | 7/2007 | Causey, III et al. |
| 2007/0180140 A1 | 8/2007 | Welch et al. |
| 2007/0216764 A1 | 9/2007 | Kwak |
| 2007/0254593 A1 | 11/2007 | Jollota et al. |
| 2007/0258395 A1 | 11/2007 | Jollota et al. |
| 2007/0276270 A1 | 11/2007 | Tran |
| 2008/0004907 A1 | 1/2008 | Bayne |
| 2008/0012761 A1 | 1/2008 | Derrick et al. |
| 2008/0071234 A1 | 3/2008 | Kelch et al. |
| 2008/0108880 A1 | 5/2008 | Young et al. |
| 2008/0281168 A1 | 11/2008 | Gibson et al. |
| 2009/0023391 A1 | 1/2009 | Falck |
| 2009/0058635 A1 | 3/2009 | LaLonde et al. |
| 2009/0105549 A1 | 4/2009 | Smith et al. |
| 2009/0128320 A1 | 5/2009 | Needham et al. |
| 2009/0184835 A1 | 7/2009 | Deaver, Sr. et al. |
| 2009/0203329 A1 | 8/2009 | White et al. |
| 2009/0247114 A1 | 10/2009 | Sennett et al. |
| 2009/0252117 A1 | 10/2009 | Sherman et al. |
| 2009/0299788 A1 | 12/2009 | Huber et al. |
| 2010/0027518 A1 | 2/2010 | Wang |
| 2010/0077115 A1 | 3/2010 | Rofougaran |
| 2010/0079276 A1 | 4/2010 | Collins et al. |
| 2010/0080200 A1 | 4/2010 | Stewart |
| 2010/0085948 A1 | 4/2010 | Yu et al. |
| 2010/0117835 A1 | 5/2010 | Nanikashvili |
| 2010/0138235 A1 | 6/2010 | Marks et al. |
| 2010/0166170 A1 * | 7/2010 | East et al. ................. 379/221.01 |
| 2010/0198142 A1 | 8/2010 | Sloan et al. |
| 2010/0217723 A1 | 8/2010 | Sauerwein, Jr. et al. |
| 2010/0219250 A1 | 9/2010 | Wang |
| 2010/0234695 A1 | 9/2010 | Morris |
| 2010/0279647 A1 | 11/2010 | Jacobs et al. |
| 2010/0317286 A1 | 12/2010 | Jung et al. |
| 2010/0318578 A1 | 12/2010 | Treu et al. |
| 2011/0021902 A1 | 1/2011 | Kim et al. |
| 2011/0032822 A1 | 2/2011 | Soomro |
| 2011/0087756 A1 | 4/2011 | Biondi et al. |
| 2011/0093297 A1 | 4/2011 | Dicks et al. |
| 2011/0148624 A1 | 6/2011 | Eaton et al. |
| 2011/0161111 A1 | 6/2011 | Dicks et al. |
| 2011/0270045 A1 | 11/2011 | Lebel et al. |
| 2011/0280224 A1 | 11/2011 | Falck et al. |
| 2011/0292862 A1 | 12/2011 | Shimizu |
| 2012/0004925 A1 | 1/2012 | Braverman et al. |
| 2012/0108917 A1 | 5/2012 | Libbus et al. |
| 2012/0182143 A1 | 7/2012 | Gaines et al. |
| 2012/0182924 A1 | 7/2012 | Gaines et al. |
| 2012/0182927 A1 | 7/2012 | Wiesner et al. |
| 2012/0184207 A1 | 7/2012 | Gaines et al. |
| 2012/0184237 A1 | 7/2012 | Gaines et al. |
| 2012/0185268 A1 | 7/2012 | Wiesner et al. |
| 2012/0226768 A1 | 9/2012 | Gaines et al. |
| 2012/0226771 A1 | 9/2012 | Harrington et al. |
| 2012/0256751 A1 | 10/2012 | Nallabelli et al. |
| 2012/0293323 A1 | 11/2012 | Kaib et al. |
| 2013/0015966 A1 | 1/2013 | Soomro et al. |
| 2013/0021169 A1 | 1/2013 | Soomro et al. |
| 2013/0022022 A1 | 1/2013 | Schmitt |
| 2013/0162426 A1 | 6/2013 | Wiesner et al. |
| 2013/0278414 A1 | 10/2013 | Sprigg et al. |
| 2014/0009271 A1 | 1/2014 | Collins et al. |

FOREIGN PATENT DOCUMENTS

| | | |
|---|---|---|
| KR | 10-2009-0122968 A | 12/2009 |
| KR | 10-2010-0028318 A | 3/2010 |
| WO | WO 94/16617 | 8/1994 |
| WO | WO 98/14228 A1 | 4/1998 |
| WO | WO 03/048919 A1 | 6/2003 |
| WO | WO 2004/070994 A2 | 8/2004 |
| WO | WO 2004/070994 A3 | 8/2004 |
| WO | WO 2005/057294 | 6/2005 |
| WO | WO 2005/057834 A2 | 6/2005 |
| WO | WO 2005/098736 A2 | 10/2005 |
| WO | WO 2008/052034 A1 | 5/2008 |
| WO | WO 2009/032134 A2 | 3/2009 |

OTHER PUBLICATIONS

Response filed Jul. 12, 2013; to Final Office Action dated May 22, 2013; for U.S. Appl. No. 13/037,886; 14 pages.

Office Action; dated May 15, 2013; for U.S. Appl. No. 13/006,784; 35 pages.

Article 19 Amendment; dated Nov. 16, 2012; for PCT Pat. App. No. PCT/US2012/021007; 7 pages.

Article 19 Amendment; dated Feb. 4, 2013; for PCT Pat. App. No. PCT/US2012/025906; 9 pages.

PCT International Preliminary Report on Patentability; dated Jul. 25, 2013; for PCT Pat. App. No. PCT/US2012/021007; 12 pages.

PCT International Search Report; dated Aug. 2, 2012; for PCT Pat. App. No. PCT/US2012/021008.

PCT International Preliminary Report on Patentability; dated Jul. 25, 2013; for PCT Pat. App. No. PCT/US2012/021008; 7 pages.

Miche, et al., "The Internet of Vehicles or the Second Generation of Telematic Services", ERCIM News, ERCIM, Paris, FR, vol. 77, Apr. 1, 2009, pp. 43-45.

Kawai et al., "Proposal of an Assured Corridor Mechanism for Urgent Information Transmission in Wireless Sensor Networks", IEICE Trans. on Commun., vol. E90B, No. 10, Oct. 1, 2007, pp. 2817-2826, XP001508610.

(56) References Cited

OTHER PUBLICATIONS

International Search Report and Written Opinion of the International Searching Authority for PCT/US2012/021007, dated Sep. 20, 2012, 19 pages.
International Search Report and Written Opinion of the International Searching Authority for PCT/US2013/020069, dated Feb. 1, 2013, 9 pages.
International Search Report and Written Opinion of the International Searching Authority for PCT/US2013/020071, dated Feb. 1, 2013, 10 pages.
International Search Report and Written Opinion of the International Searching Authority for PCT/US2012/025906, dated Dec. 3, 2012, 21 pages.
Office Action dated Nov. 16, 2012 for U.S. Appl. No. 13/037,886, filed Mar. 1, 2011, 19 pages.
Response to Office Action dated Nov. 16, 2012 for U.S. Appl. No. 13/037,886, filed Feb. 15, 2013.
Atmel Corporation, "ZigBee PRO Stack and Software Development Kit," http://www.meshnetics.com/wsn-software/, Nov. 4, 2011.
Bacheldor, "Hospital Tries ZigBee to Track Patients," RFID Journal, Jul. 21, 2006.
BelAir Networks, "Capacity of Wireless Mesh Networks," white paper, 2006.
Bogia, "Enabling the future of u-Health-IEEE 11073 Personal Health Device Standards," slides, Sep. 16, 2009.
Bowman, "Newly Ratified ZigBee Health Care Profile Now Available for Public Download," http://www.fiercehealthcare.com/node/40708, Apr. 6, 2010.
Craig, "ZigBee Networks," http://medicaldesign.com/electrical-components/zigbee_networks/, Apr. 1, 2005.
Craig, "ZigBee: 'Wireless Control That Simply Works'," https://docs.zigbee.org/zigbee-docs/dcn/04-1427.pdf, prior to Jan. 2011.
Digi International Inc., "ConnectPort® X4 H," retrieved from the Internet: http://www.digi.com, 2008-2010.
Digi International Inc., "Demystifying 802.15.4 and ZigBee®," white paper, retrieved from the Internet: http://www.digi.com, 2008-2010.
Digi International Inc., "XBee® & XBee-PRO® ZB," retrieved from the Internet: http://www.digi.com, 2008-2010.
Digi International Inc., "XBee® & XBee-PRO® ZB ZigBee® PRO RF Modules," http://www.digi.com/products/wireless/zigbee-mesh/xbee-zb-module.jsp, Nov. 2, 2010.
Dvorak, "Remote Monitoring," http://medicaldesign.com/electrical-components/remote_monitoring/index.html, Apr. 1, 2005.
ENP Newswire, "Freescale products achieve ZigBee Health Care Certification," May 19, 2010.
Huang, "Medical electronics: from hospital and clinic to the home," http://www.eetimes.com/General/DisplayPrintViewContent?contentItemid=4211247, Dec. 8, 2010.
ICP DAS, "ZigBee Converter User's Manual," Sep. 22, 2008.
Le, "Designing a ZigBee-ready IEEE 802.15.4-compliant radio transceiver," http://rfdesign.com/mag/411rfdf4.pdf, Nov. 2004.
Norris et al., "Single-chip ZigBee for Indoor Mobile Telemetry," presentation, Jun. 21, 2005.
Pinto, "WMM-Wireless Mesh Monitoring," Technical report, 2009.
Sailhan et al., "Wireless Mesh Network Monitoring: Design, Implementation and Experiments," In proc. of IEEE Workshop on Distributed Autonomous Network Management (DANMS), 2007.
Skibniewski et al, "Ubiquitous Computing: Object Tracking and Monitoring Inconstruction Processes Utilizing Zigbee™ Networks," The 23th International Symposium on Automation and Robotics in Construction (ISARC2006), Oct. 3-5, Tokyo, Japan.
Stewart, "Build reliable Zigbee-based solutions," EE Times-Asia, Apr. 16-30, 2007.
Texas Instruments, "Choose your ZigBee solution with TI," 1Q 2010.
Texas Instruments, "Consumer Medical Applications Guide," retrieved from the Internet: http://www.ti.com/medical, 2010.
Texas Instruments, "RF/IF and ZigBee® Solutions," http://focus.ti.com/analog/docs/gencontent.tsp? familyid=367&genContentid=24190&DC . . . , Dec. 8, 2010.
Texas Instruments, "ZigBee® Wireless Networking Overview," 1 page, 2010.
The Silicon Horizon Inc., "techFX Zigbee rev A-techFX Zigbee Tools v 1.0," 2007-2008.
Tutorial-Reports.com, "Zigbee Tutorial," http://www.tutorial-reports.com/book/print/152, Nov. 1, 2010.
Unknown author, "The Nokia Network Monitor Introduction," http://www.panuworld.net/nuukiaworld/misc/netmon/index.htm, Oct. 30, 2005.
Versel, "ZigBee Alliance ratifies wireless protocol for low-power medical devices," retrieved from the Internet: http://www.fiercemobilehealthcare.com, Apr. 6, 2010.
Wellspring, "Router, Gateway, Base Station, Cell Modem Specification and Submittal," http://www.h2odegree.com/documents/ReferenceLibrary/OtherProductLiterature/RouterGatewayBaseSpecSheetSubmittal.pdf, 5 pages, prior to Jan. 2011.
Wellspring, "Wellspring Switches to a ZigBee-Cellular Hybrid System," press release, Feb. 20, 2006.
ZigBee Alliance, "ZigBee Wireless Sensor Applications for Health, Wellness and Fitness," https://docs.zigbee.org/zigbee-docs/dcn/09-4962.pdf, Mar. 2009.
Office Action; dated May 15, 2013; for U.S. Appl. No. 13/006,784; 37 pages.
Office Action dated May 22, 2013; for U.S. Appl. No. 13/037,886; 14 pages.
PCT Search Report and Written Opinion of the ISA; dated Mar. 15, 2013; for PCT Pat App. No. PCT/US2012/068895, dated, 15 pages.
PCT Search Report and Written Opinion of the ISA; dated Apr. 1, 2013; for PCT Pat. App. No. PCT/US2012/068892; 12 pages.
PCT Search Report and Written Opinion of the ISA; dated Apr. 1, 2013; for PCT Pat. App. No. PCT/US2012/068888; 15 pages.
PCT Search Report and Written Opinion of the ISA; dated Apr. 29, 2013; for PCT Pat. App. No. PCT/US2013/021530; 10 pages.
Request for Continued Examination filed on Jan. 24, 2014; for U.S. Appl. No. 13/037,886; 2 pages.
Response filed Feb. 13, 2014; to Office Action dated Sep. 5, 2013; for U.S. Appl. No. 13/006,769; 16 pages.
Response filed Feb. 13, 2014; to Office Action dated Dec. 2, 2013; for U.S. Appl. No. 13/006,784; 19 pages.
Response filed Feb. 13, 2014 for Office Action dated Sep. 5, 2013 for U.S. Appl. No. 13/006,769; 18 pages.
European Response filed Mar. 3, 2014; to Official Communication dated Aug. 22, 2013; and to the Written Opinion; for European Pat. App. No. 12704944.3; 15 pages.
European Response filed Mar. 3, 2014; to Official Communication dated Aug. 22, 2013; and to the Written Opinion; for European Pat. App. No. 12701584.0; 11 pages.
PCT Search Report and Written Opinion of the ISA dated Mar. 4, 2014; for PCT Pat. App. No. PCT/US2013/059703; 12 pages.
Office Action dated Sep. 5, 2013, for U.S. Appl. No. 13/006,769, 36 pages.
Notice of Allowance; dated Oct. 9, 2013; for U.S. Appl. No. 13/037,886; 11 pages.
Response filed Aug. 14, 2013; to Office Action dated May 15, 2013; for U.S. Appl. No. 13/006,784; 13 pages.
Office Acton dated Dec. 27, 2013; for U.S. Appl. No. 13/352,575; 31 pages.
Amendment filed Mar. 26, 2014, to Office Action dated Dec. 27, 2013; for U.S. Appl. No. 13/352,575; 12 pages.
Amendment filed Mar. 26, 2014; to Office Action dated Jan. 7, 2014; for U.S. Appl. No. 13/353,565; 15 pages.
Amendment and Response to Restriction Requirement for Office Action dated Feb. 10, 2014; filed Mar. 21, 2014; for U.S. Appl. No. 13/352,608; 7 pages.
Letter from CCPIT Patent and Trademark Law Office dated Mar. 3, 2014; for Chinese Pat. App. No. 201280011025.0; 1 page.
Chinese Voluntary Amendment (including English translation) received Mar. 3, 2014; for Chinese Pat. App. No. 201280011025.0; 16 pages.

(56) References Cited

OTHER PUBLICATIONS

European Comments on Written Opinion dated Nov. 8, 2013; for EP Pat. App. No. 12708203.0; 2 pages.
Final Office Action dated Dec. 2, 2013; for U.S. Appl. No. 13/006,784; 38 pages.
Office Action dated Jan. 7, 2014; for U.S. Appl. No. 13/353,565; 33 pages.
Office Action dated May 27, 2014; for U.S. Appl. No. 13/334,463; 48 pages.
Office Action dated Apr. 29, 2014; for U.S. Appl. No. 13/352,608; 50 pages.
Responses to Office Action dated Apr. 29, 2014; for U.S. Appl. No. 13/352,608; 11 pages.
Mexican Official Action recieved May 2, 2014, for Mexican Pat. App. No. MX/A2013/008157; 3 pages.
Mexican Notice of Allowance dated May 7, 2014; for Mexican Pat. App. No. MX/a/2013/009985; 2 pages.
Mexican Office Action recieved Apr. 22, 2014; for Mexican Pat. App. No. MX/a/2013/008154; 4 pages.

* cited by examiner

WIRELESS RELAY MODULE FOR REMOTE MONITORING SYSTEMS

RELATED APPLICATION

This application is a continuation-in-part application claiming priority of U.S. patent application Ser. No. 13/006,769 entitled "Wireless Relay Module for Remote Monitoring Systems filed Jan. 14, 2011", that is related to U.S. application Ser. No. 13/006,784, filed Jan. 14, 2011, entitled "Medical Device Wireless Network Architectures", which are both incorporated by reference in therein entirety herein.

FIELD OF THE INVENTION

The present application is directed to a wireless relay module for communicating between a series of medical devices and remote monitoring devices, and more particularly, to a wireless relay module for receiving communications from and transmitting communications to medical devices via one or more wireless relay networks, and for transferring the communications received from the remote monitoring devices via one or more internet-accessible wireless communications networks.

BACKGROUND OF THE INVENTION

In critical care and home care health service centers including hospitals, clinics, assisted living centers and the like, care giver-patient interaction time is at a premium. Moreover, response times by care givers to significant health conditions and events can be critical. Systems of centralized monitoring have been developed to better manage care giver time and patient interaction. In such systems, physiological data from each patient is transmitted to a centralized location. At this centralized location, a single or small number of technicians monitor all of this patient information to determine patient status. Information indicating a patient alarm condition will cause the technicians and/or system to communicate with local care givers to provide immediate patient attention, for example via wireless pagers and/or cell phones, and/or by making a facility-wide audio page.

Implementing such centralized monitoring systems using wireless networks may present a number of difficulties. In order to effectively monitor patient status using information provided by a variety of medical devices that may be dynamically assigned to patients in a variety of rooms and on a variety of floors in a facility, it would be desirable to establish communications between the medical devices and the centralized location by means of a local area network such as, for example, a "WiFi" network based on IEEE 802.11 standards. However, as such networks are typically already in place in facilities to support a variety of other functions (for example, physician access to electronic medical records (EMRs), facility administrative systems and other functions), it is often undesirable to secure sufficient local area network access for the purpose of providing centralized monitoring. Moreover, when a patient is located remotely from a critical care health service center (for example, at home), access to traditional local area network facilities such as a WiFi network may be unavailable or not sufficiently reliable to support critical care monitoring applications.

Clearly, for improved efficiencies in centralized monitoring of critical care and home care health service centers, it may be desirable to provide a single "off-site" centralized monitoring location for monitoring several geographically-dispersed critical care health service centers.

As an alternative to conventional WiFi or IEEE 801.11-based local area networks, ZIGBEE networks based on the IEEE 802.15.4 standard for wireless personal area networks have been used for collecting information from a variety of medical devices in accordance with IEEE 11073 Device Specializations for point-of-care medical device communication, including for example pulse oximeters, blood pressure monitors, pulse monitors, weight scales and glucose meters. See, e.g., *ZIGBEE Wireless Sensor Applications for Health, Wellness and Fitness*, the ZIGBEE Alliance, March 2009, which is incorporated by reference herein in its entirety. ZIGBEE networks provide the advantage of being dynamically configurable, for example, in "self-healing" mesh configurations, and operating with low power requirements (enabling, for example, ZIGBEE transceivers to be integrally coupled to the medical devices under battery power). However, transmission ranges between individual ZIGBEE transceivers are generally limited to no more than several hundred feet. As a consequence, such networks are unusable for centralized monitoring locations located off-site. Also, in accordance with applicable patient data privacy provisions of the Health Insurance Portability and Accountability Act of 1996 (HIPAA), communication of information between the monitored medical devices and the central monitoring location must be done securely.

Thus, it would be desirable to provide a wireless relay module capable of relaying communications made between medical devices in communication with a wireless local area network or wireless personal area network and a remote monitoring device in communication with a wireless network of wider reach (for example, a wireless wide area network).

SUMMARY OF THE INVENTION

The present invention is directed to a wireless relay module for providing networked communications between a series of medical devices and remote monitoring devices. In accordance with a preferred embodiment of the invention, one or more medical devices (including but not limited to including for example, respirators, external feeding devices, pulse oximeters, blood pressure monitors, pulse monitors, weight scales and glucose meters) are provided at a patient facility. An interface circuit is coupled to each medical device, and is configured for communicating with one of a plurality of the wireless relay modules via one of a plurality wireless relay networks. The wireless relay modules are advantageously further configured to communicate with a remote monitoring device over one or more internet-accessible wireless communication networks, and preferably, wireless wide-area networks (WWAN) such as a mobile telephone data network including (for example, based on a Global System for Mobile Communications (GSM) or Code Division Multiple Access (CDMA) cellular network or associated wireless data channels, or WiMAX networks). Also, for compliance for example with HIPAA regulations, communications over each of the wireless networks are preferably conducted securely using, for example, encryption of data and/or commands.

Each of the plurality of wireless relay modules includes a receiver capable of wirelessly receiving medical device data from respective interface circuits via the wireless relay network, a first transmitter capable of wirelessly transmitting medical device data to another one of the wireless relay modules over the wireless relay network, second and third transmitters capable of wirelessly transmitting data over respective internet-accessible wireless communications networks, and a controller coupled to the first, second and third transmitters.

The controller is configured to determine access status of the respective internet-accessible wireless communications networks, and to select one of the first, second or third transmitters based on that status and routing criteria. For example, when the status indicates that the first or second internet-accessible wireless communications networks is accessible to the wireless relay module, the controller in accordance with the status selects the first or second transmitter for transmitting medical device data transmitted by the interface circuit to the wireless relay module. If both the first and second internet-accessible wireless communications networks are accessible to the wireless relay module, the controller selects either the first or second transmitter for transmitting medical device data in accordance with routing criteria. Such routing criteria may give priority to the internet-accessible wireless communications networks of the greatest signal strength or of lower cost or as specified by a network manager.

When the status indicates that neither internet-accessible wireless communications network is accessible, the controller selects the third transmitter for transmitting the medical device data to another one of the wireless relay modules. In this manner, another attempt to transmit the medical device data over one of the internet-accessible wireless communication networks can be attempted by this other wireless relay module (and potentially additional ones of the wireless relay modules) until a successful transmission is achieved. In addition, it should be understood that additional receivers and transmitters may be employed in the module to communicate with different medical devices over different wireless relay networks.

Each of the plurality of wireless relay modules may also include additional receivers for receiving communications from the internet-accessible wireless communications networks.

BRIEF DESCRIPTION OF THE DRAWINGS

The invention will become more readily apparent from the Detailed Description of the Invention, which proceeds with reference to the drawings, in which.

DETAILED DESCRIPTION OF THE INVENTION

Reference will now be made in detail to exemplary embodiments of the invention, including the best modes contemplated by the inventors for carrying out the invention. Examples of these exemplary embodiments are illustrated in the accompanying drawings. While the invention is described in conjunction with these embodiments, it will be understood that it is not intended to limit the invention to the described embodiments. Rather, the invention is also intended to cover alternatives, modifications, and equivalents as may be included within the spirit and scope of the invention as defined by the appended claims.

In the following description, specific details are set forth in order to provide a thorough understanding of the present invention. The present invention may be practiced without some or all of these specific details. In other instances, well-known aspects have not been described in detail in order not to unnecessarily obscure the present invention.

For the purpose of illustrating the present invention, exemplary embodiments are described with reference to FIGS. 1-5.

In this specification and the appended claims, the singular forms "a," "an," and "the" include plural references unless the context clearly dictates otherwise. Unless defined otherwise, all technical and scientific terms used herein have the same meaning as commonly understood to one of ordinary skill in the art to which this invention belongs.

Figure 1:
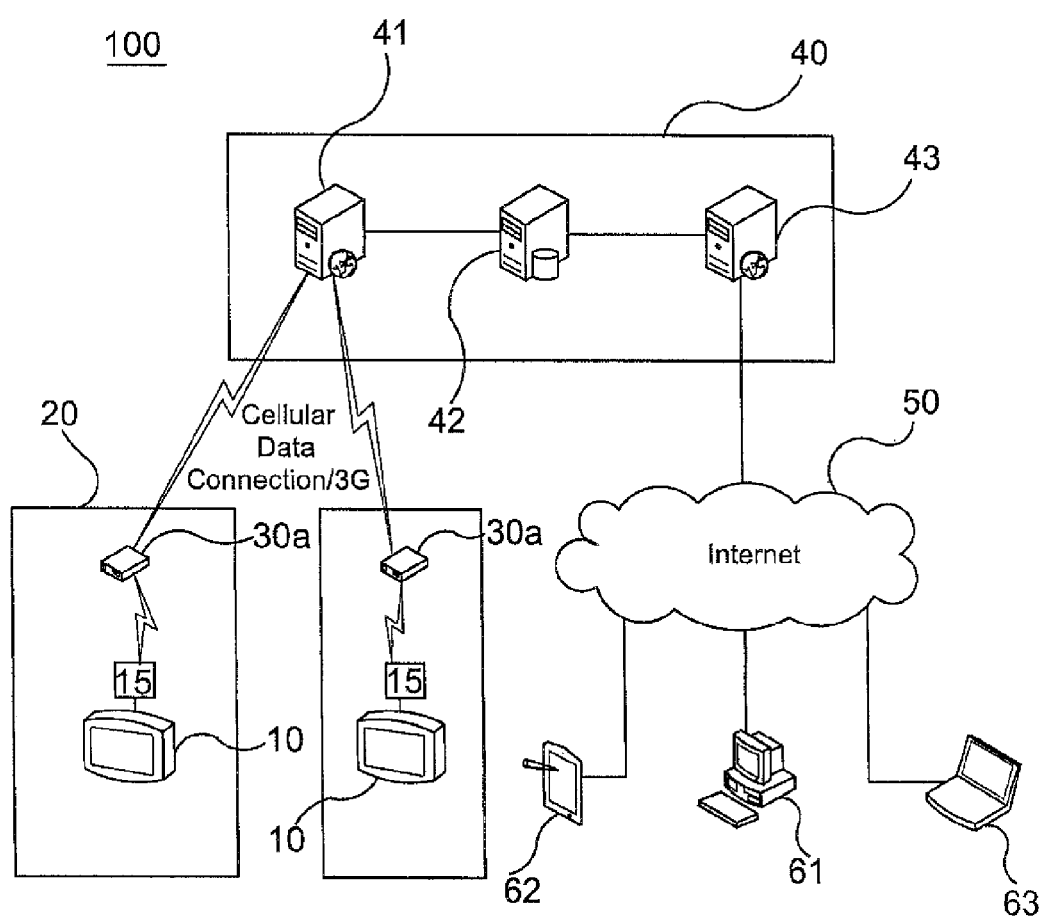
FIG. 1 presents a block diagram of an exemplary medical device network architecture that incorporates a wireless relay module according to the present invention.

A diagram of an exemplary architecture 100 for a system for monitoring medical devices in accordance with the present invention is illustrated in FIG. 1. One or more medical devices 10 are provided at a patient facility 20 for monitoring the medical condition and/or administering medical treatment to one or more patients. Patient facility 20 may comprise a critical care health service center (for example, including hospitals, clinics, assisted living centers and the like) servicing a number of patients, a home facility for servicing one or more patients, or a personal enclosure (for example, a backpack) that may attached to or worn by an ambulatory patient.

Associated with each medical device 10 is an interface circuit 15 that includes a transceiver having one or more of a transmitter and/or a receiver for respectively transmitting and receiving signals in a facility-oriented wireless network such as, for example, a Low-Rate Wireless Personal Area Networks or "LR-WPAN," ZIGBEE network or another low-power personal area network such as a low power BLUETOOTH network, existing or presently under development or consideration. See, e.g., Houda Labiod et al., *Wi-Fi, Bluetooth, Zigbee and WiMax*, Springer 2010, which is incorporated by reference herein in its entirety. It should be understood that interface circuit 15 may be contained within or disposed external to medical device 10 in accordance with the present invention. Also provided within the patient facility 20 are one or more relay modules 30a.

Figure 3A:
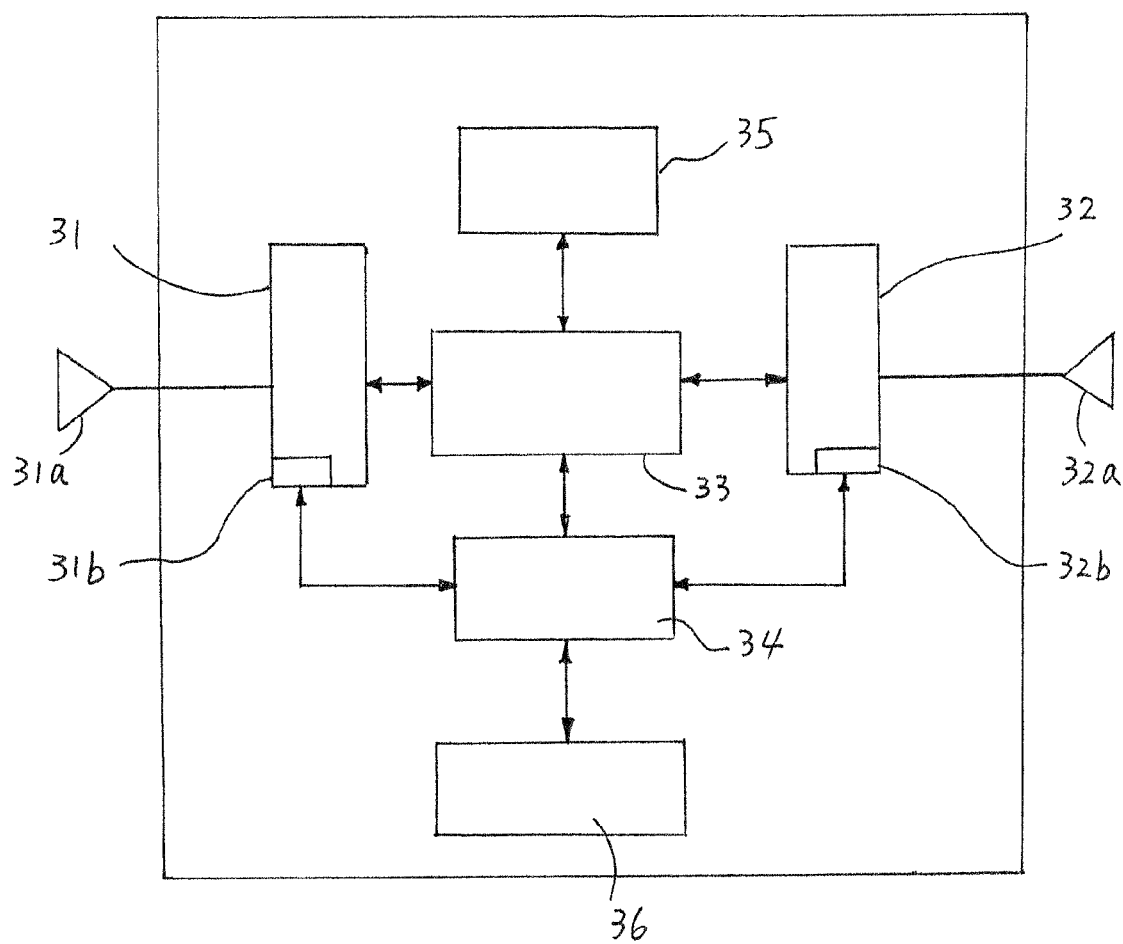
FIG. 3(a) presents a schematic diagram illustrating an exemplary wireless relay module according to the present invention.

As described in greater detail with regard to FIG. 3(a), each module 30a includes a first transceiver for receiving signals from and transmitting signals to the interface circuits 15 in one or more of the facility-oriented wireless networks. Each relay module 30a, as depicted in FIG. 3(a), further includes a second transceiver for wirelessly transmitting signals to and receiving signals from an access point 40 via a wireless wide-area network or "WWAN". Suitable WWANs for use with the present invention include, for example, networks based on a Global System for Mobile Communications (GSM) or Code Division Multiple Access (CDMA) cellular network or associated with the 2G, 3G, 3G Long Term Evolution, 4G, WiMAX cellular wireless standards of the International Telecommunication Union Radiocommunication Sector (ITU-R). See, e.g., Vijay Garg, *Wireless Communications & Networking*, Morgan Kaufmann 2007, which is incorporated by reference herein in its entirety. Additional suitable exemplary WWANs include metropolitan area networks (MANs), campus area networks (CANs), local area networks (LANs), home area networks (HANs), personal area networks (PANs) and body area networks (BANs). It should be readily understood that the relay module 30a may include additional transceivers for communicating with additional WWANs or additional facility-oriented wireless networks as described in greater detail with respect to FIG. 6.

For compliance with HIPAA regulations, communications over each of the facility-oriented wireless network and WWAN are preferably conducted securely using, for example, encryption, a Secure Sockets Layer (SSL) protocol or a Transport Layer Security (TLS) protocol.

As illustrated in FIG. 1, a suitable access point 40 useable with the present invention may include an inbound web server 41 that incorporates or otherwise has access to a transceiver for communicating with the relay modules 30a over a particular WWAN. Medical device data received by the inbound web server 41 over the WWAN is forwarded to a secure data storage server 42, which is configured for example to log the received data in association with identification information of the associated medical devices. An outbound web server 43 is configured, for example, to receive and qualify data retrieval requests submitted by one or more of remote monitoring devices 61, 62 and 63 over a broad-band network 50 (for example, over the Internet), to request associated medical device data to be retrieved from the secure data storage server 42, and to format and transmit the retrieved data to the one or more remote monitoring devices 61, 62 and 63 for display on associated device displays. It should be understood that any architecture for the access point 40 that enables the receipt, storage and retrieval of medical device data on a device display of the one or more remote monitoring devices 61, 62 and 63 is suitable for use in conjunction with the present invention.

Figure 2:
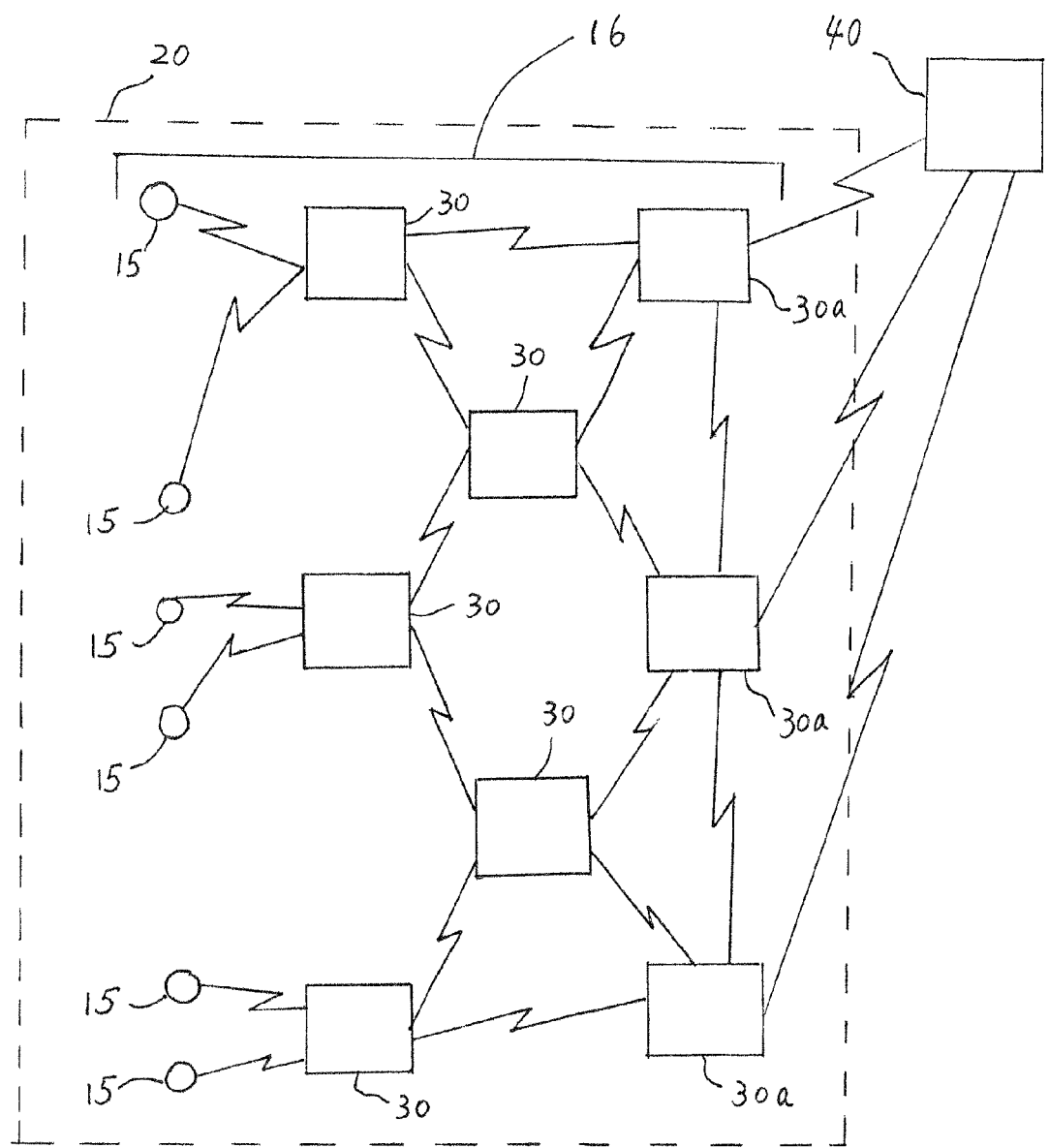
FIG. 2 presents a block diagram further illustrating exemplary wireless network components of the architecture according to FIG. 1.

FIG. 2 presents a block diagram that further illustrates exemplary components of the inventive architecture that are located within or otherwise associated with the patient facility 20 of FIG. 1. In FIG. 2, a number of interface circuits 15 and relay modules 30, 30a are arranged in a single wireless relay network 16 within the patient facility 20 for illustration purposes only. It should be understood that other interface circuits 15 and relay modules 30, 30a may communicate over other wireless relay networks similar to network 16 in the patient facility 20. In FIG. 2, The interface circuits 15 and relay modules 30, 30a are configured to communicate with one another via associated wireless links. In a preferred embodiment of the present invention represented in FIG. 2, the network 16 is a ZIGBEE mesh network based on IEEE 802.15.4. However, the wireless relay network 16 or additional wireless relay networks in the patient facility may be organized according to a variety of other wireless local area network (WLAN) or WPAN formats including, for example, WiFi WLANs based on IEEE 802.11 and BLUETOOTH WPANs based on IEEE 802.15.1.

In the illustrated wireless relay network 16, each of the interface circuits 15 includes a communications interface such as, for example, a wired communications interface, to an associated medical device 10. In addition, each of the relay modules 30, 30a includes at least one transceiver configured to communicate with other relay modules 30, 30a in the wireless relay network 16. Relay modules 30a further include at least a second transceiver for communicating over the WWAN with the access point 40.

The use of a ZIGBEE mesh network for network 16 provides the advantages of being self-configurable when one or more interface circuits 15 and/or relay modules 30, 30a are added to the network, and self-healing when one or more interface circuits 15 and/or relay modules 30, 30a are removed from or otherwise disabled in the network. Sub-groupings of the interface circuits 15 and relay modules 30, 30a may be provided in a defined geographic space (for example, on an individual floor or within a region of a floor in a multi-floor home or care facility).

FIG. 3(a) provides a block diagram illustrating exemplary components of relay module 30a. The relay module 30a of FIG. 3(a) includes a first transceiver 31 for wirelessly communicating with interface circuits 15 and other relay modules 30, 30a in the WLAN or WPAN network 16 of FIG. 2 via an antenna 31a. The relay module 30a further includes a second transceiver 32 for wirelessly communicating with the access point 40 over the WWAN via an antenna 32a. Each of the transceivers 31, 32 is in communication with a data processing circuit 33, which is configured to operate under the control of a controller, e.g., processor, 34 to accept data received by the transceivers 31, 32 and store the received data in a memory such as buffer element 35. In addition, the data processing circuit 33 is further configured to retrieve data from the buffer element 35 under the direction of the processor 34 and provide the retrieved data to a selected one of the transceiver 31 or transceiver 32 for transmission. In order to make a selection, the processor 34 is configured to communicate with respective status modules 31b, 32b of the transceivers 31, 32 in order to determine a communications status of each of the transceivers 31, 32.

The processor 34 is also preferably in communication with an input/output circuit 36, which provides signals to one or more display elements of the relay module 30a, for example, for indicating a start-up or current status of the relay module 30a, including communication or connection status with the WLAN or WPAN network 16 and WWAN. Input/output circuit 36 may also be configured to provide signals to indicate an A/C power loss, and or to be responsive to signals provided by one or more input devices provided in proximity to the one or more display elements.

Relay module 30a may preferably be provided as a small physical enclosure with an integral power plug and power supply circuit, such that the relay module 30a may be directly plugged into and supported by a conventional wall outlet providing commercial A/C power. Relay module 30a may also preferably include a battery back-up circuit (not shown) to provide uninterrupted power in the event of A/C power outage of short duration. Battery back-up may also be advantageous, for example, for using the relay module 30a in an ambulatory mode that enables the patient to move within and potentially at a distance from the facility 20, for example, with a medical device 10 that is a portable feeding device. In this configuration, for example, the medical device 10, the interface circuit 15 and relay module 30 may be conveniently carried in a patient-wearable backpack.

FIGS. 3(b)-3(d) respectively illustrate top, front and side views of an exemplary configuration 37 for the relay module 30a. Configuration 37 includes a housing 37a, which is shown in FIGS. 3(b)-3(d) configured essentially as a rectangular box or prism. It should however be noted that the housing may alternatively be configured in any of a variety of three-dimensional shapes having a sufficient interior volume for housing the associated circuits, having a sufficient area 37c on a front panel 37b of the housing 37a for locating a control panel 38 (as further illustrated in FIG. 3(e)), and having a sufficient area on a rear panel 37d for providing a receptacle support 37e and power plug 37f for supportably plugging the module configuration 37 into a conventional power outlet. The power plug 37f may also be provided in a modular and replaceable removable configuration enabling power plugs 37*f* to be configured according to a variety of international standards to be easily provided to the configuration 37.

Figure 3:
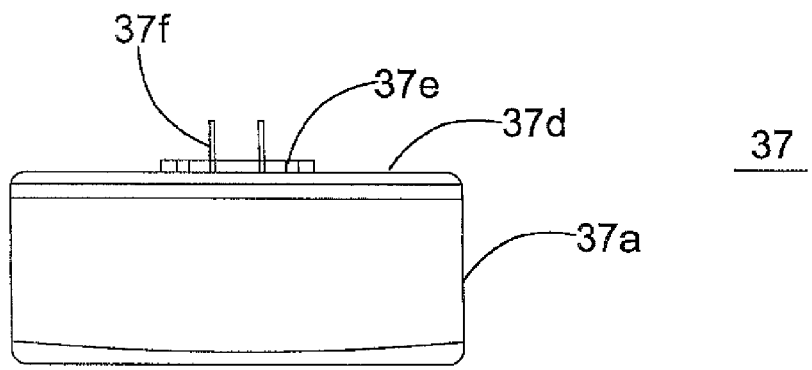
FIGS. 3(b)-3(d) present schematic diagrams respectively illustrating top, front and side views of an embodiment of the wireless relay module of FIG. 3(a)
FIG. 3(e) illustrates an exemplary control panel for the wireless relay module of FIGS. 3(b)-3(d)
Figure 3:
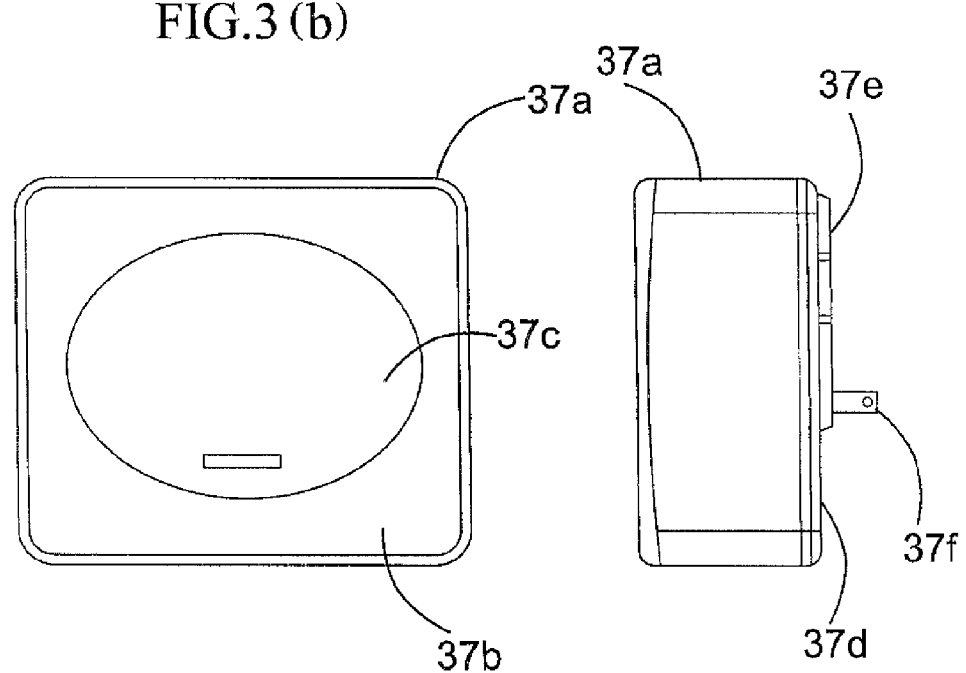

FIG. 3(*e*) illustrates an exemplary control panel 38 of module configuration 37. The exemplary control panel 38 preferably includes, for example, a power switch 38*a* for powering and/or de-powering the module configuration 37 after it has been plugged into the conventional wall outlet or equipped with a charged battery back-up subsystem. In addition, the control panel 38 preferably includes an alarm switch 38*b* which allows a user to mute and/or de-mute an audible alarm (for example, a conventional buzzer, not shown) which is coupled to an alarm circuit (not shown) that is configured to issue an alarm when A/C power to the module configuration 37 has been interrupted. The control panel 38 also includes an A/C power indicator 38*c* which may preferably be provided as one or more light-emitting diode (LED) indicator segments which are activated when A/C power has been provided to the module configuration 37. Optionally, the indicator 38*c* may be intermittently activated when A/C power is lost (for example, by means of back-up battery power) to signal the loss of A/C power.

The exemplary control panel 38 of FIG. 3(*e*) also includes a battery indicator 38*d* to indicate a status of the battery back-up circuit. For example, and as illustrated in FIG. 3(*e*), the battery indicator 38*d* may preferably include indicator segments 38*h* which may be selectively activated to indicate a capacity of the back-up battery. Indicator segments 38*h* may also be preferably provided as LED segments. Each of the segments 38*h* may, for example, be activated to indicate that the back-up battery is fully charged, and ones of the segments 38*h* may be progressively deactivated (for example, proceeding downwardly from an uppermost one of the segments 38*h*) as battery power is drawn down. In the event that remaining battery power is insufficient to operate the module configuration 37, each of the segments 38 may be deactivated. Alternatively, the indicator segments 38*h* may be provided as multicolor LED segments (for example, red and green), and ones of the segments 38*h* be illuminated as green and progressively deactivated until reaching a first low power threshold, and then illuminated as red and progressively activated as power is further diminished so that all LED segments are illuminated when battery power is no longer sufficient to power the module configuration 37.

As further illustrated in FIG. 3(*e*), the control panel 38 may further include an indicator 38*e* to indicate a status of the WLAN or WPAN network 16. Similarly to the A/C power indicator 38*c*, the WLAN/WPAN network status indicator 38*e* may be activated when the WLAN/WPAN network status is active or accessible, and either de-activated or intermittently activated when the WLAN/WPAN network status is inactive or inaccessible. Finally, a WWAN indicator 38*j* may be provided to indicate a status of access to the WWAN network. As depicted in FIG. 3(*e*), the indicator 38*j* includes indicator elements 38*f*, 38*g* for indicating the WWAN network status. In this configuration, for example, the indicator element 38*f* may be configured with a green LED indicator element that is activated when the WWAN network status is active or accessible, and the indicator 38*g* may be configured with a red LED indicator element that is activated when the WWAN network is inactive or inaccessible (for example, when a signal strength of the WWAN network available to the module configuration 37 is insufficient to support communications). Optionally, the indicator element 38*f* may be intermittently activated when the signal strength of the WWAN network available to the module configuration 37 is marginally sufficient to support communications. Indicators of the module configuration 37 such as indicators 38*a*-38*j* may be electrically connected to the input-output circuit 36 depicted in FIG. 3(*a*).

In addition, the control panel 38 may optionally include microphone and speaker elements (not shown) that enable the module configuration 37 to be operated in a voice communication mode to allow for voice communication, for example, between an operator and a help desk technician in event of a trouble condition reported by one of the medical devices 10. Alternatively or in addition, the control panel 38 may include one or more of a camera element (not shown) and/or a display element (not shown) to be operated in a visual communication mode. For example, the camera element may be used to transfer images from displays of one or more medical devices 10 to one of the remote monitoring devices 61, 62 and 63 of FIG. 1.

Figure 4:
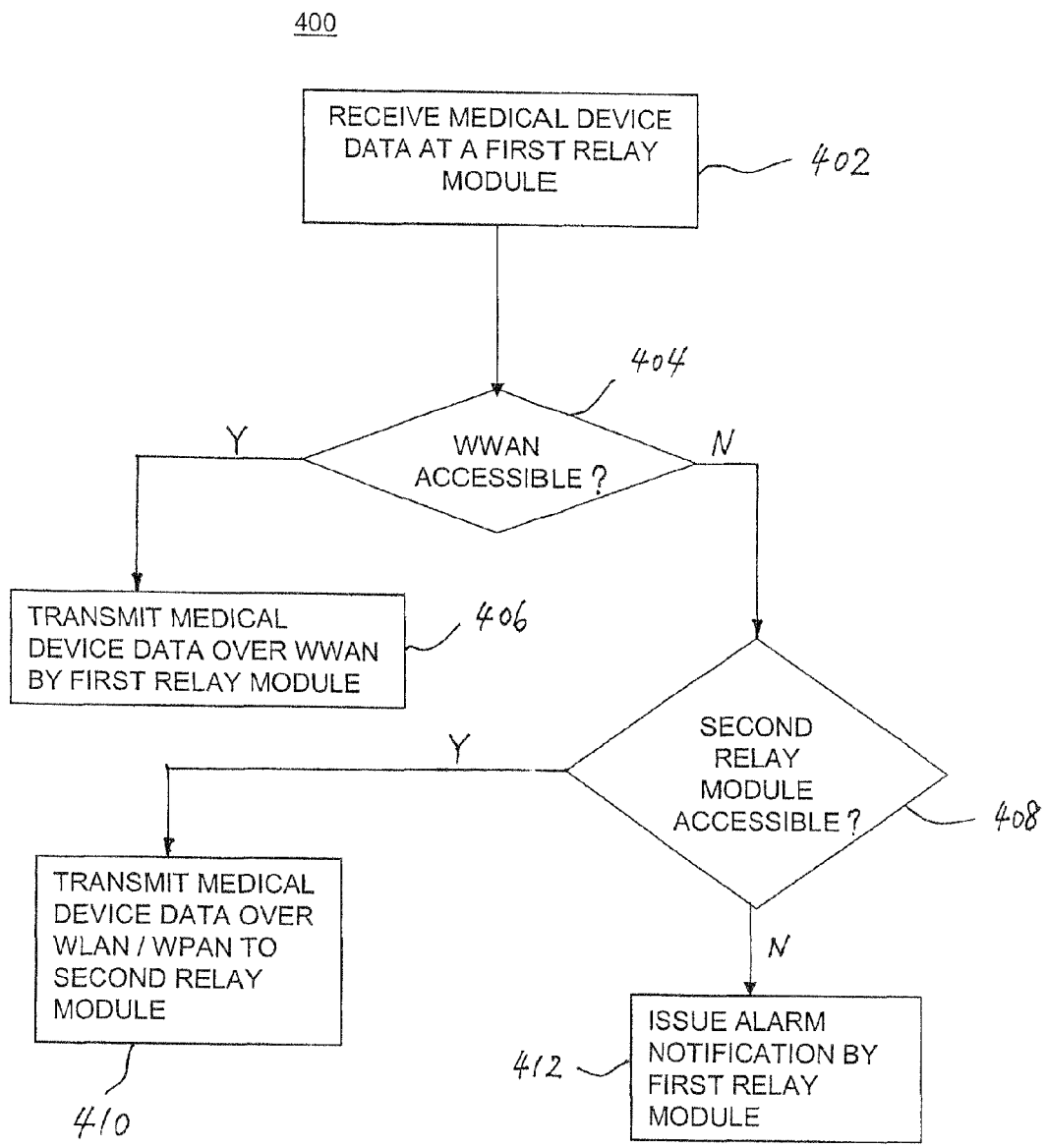
FIG. 4 presents a flow diagram illustrating a first exemplary method of operation for the relay module of FIG. 3(a)

FIG. 4 presents a flow diagram 400 illustrating an exemplary method of operation for the architecture according to FIG. 1 and relay module 30, 30*a* components of FIGS. 2 and 3(*a*), relating to the transmission of medical device data obtained from a medical device 10 to the access point 40. First, at step 402 of the method 400, the medical device data is received at a first one of the relay modules 30*a* from one of the interface circuits 15 and/or other relay modules 30, 30*a* over the wireless relay network 16. At step 404, the processor 34 of the one relay module 30*a* determines whether the WWAN is accessible by that relay module 30*a*.

The determination of step 404 may be carried out in a variety of manners. For example, the processor 34 may interrogate the status module 32*b* of the transceiver 32 at the time of the receipt of the medical device data to determine a status parameter indicative of access for the transceiver 32 to the WWAN (for example, as the result of the transceiver 32 detecting an access signal of the WWAN having adequate signal strength). Alternatively, the processor 34 may interrogate the status module 32*b* at a different time including, for example, at system start-up and/or periodically (for example, hourly), and maintain a status indicator such as in the buffer 35 or another storage element to be retrieved at the time of receipt of the medical data. As yet another alternative, the relay module 30, 30*a* may be assigned a predetermined, fixed role within the network 16. For example, relay modules 30*a* in the network 16 may be assigned a data routing assignments by a controller or "master" relay module. By definition, the WWAN status for relay module 30 that does not possess WWAN access capability shall have a fixed status of "WWAN inaccessible."

If, as provided for in step 404, the status module 32*b* indicates that the WWAN is accessible by the transceiver 32, the processor 34 will proceed to step 406 to instruct the data processing circuit 33 of the one relay module 30 to retrieve the medical device data from the buffer 35 (as necessary) and forward the medical device data to the transceiver 32 for transmission to the access point 40 over the WWAN.

Alternatively, in step 404, the status module 32*b* may indicate that the WWAN is not accessible by the transceiver 32. For example, if the one relay module 30*a* is located on a basement floor of the building in an area that is substantially shielded with respect to WWAN signals, the WWAN may not be accessible to the one relay module 30*a*. In this event, at step 408, the processor 34 determines whether a second relay module 30*a* is accessible via the WLAN or WPAN. Again, this determination may be made in a variety of manners including by instructing the transceiver 31 to send a handshake signal transmission directed to a second relay module 30*a* and to listen for a reply, or by retrieving a stored status indicator for the second relay module 30*a*.

If the second relay module 30a is accessible, then the processor 34 instructs the data processing circuit 33 of the one relay module 30a to retrieve the medical device data from the buffer 35 (as necessary) and forward the medical device data to the transceiver 31 for transmission to the second relay module 30a over the WLAN or WPAN at step 410. Alternatively, if the second relay module 30a is inaccessible in step 408, this portion of the process 400 may preferably be repeated to search for a further relay module 30a that is accessible. Alternatively, or in the event that no other relay module 30a is available, the processor 34 of the one relay module 30a may preferably issue an alarm notification at step 412. Such an alarm notification may, for example, include one or more of local visual and audio alarms as directed by processor 34 via the input/output circuit 36 of the one relay module 30a, alarm messages directed by the processor 34 to another accessible WPAN, WLAN or WWAN via one or more of the transceivers 31, 32, and/or alarm messages generated by the inbound web server 41 of the access point 40 of FIG. 1 after a specified time period has been exceeded during which a handshake signal of the relay module 30a is due to be received at the inbound web server 41.

Figure 5:
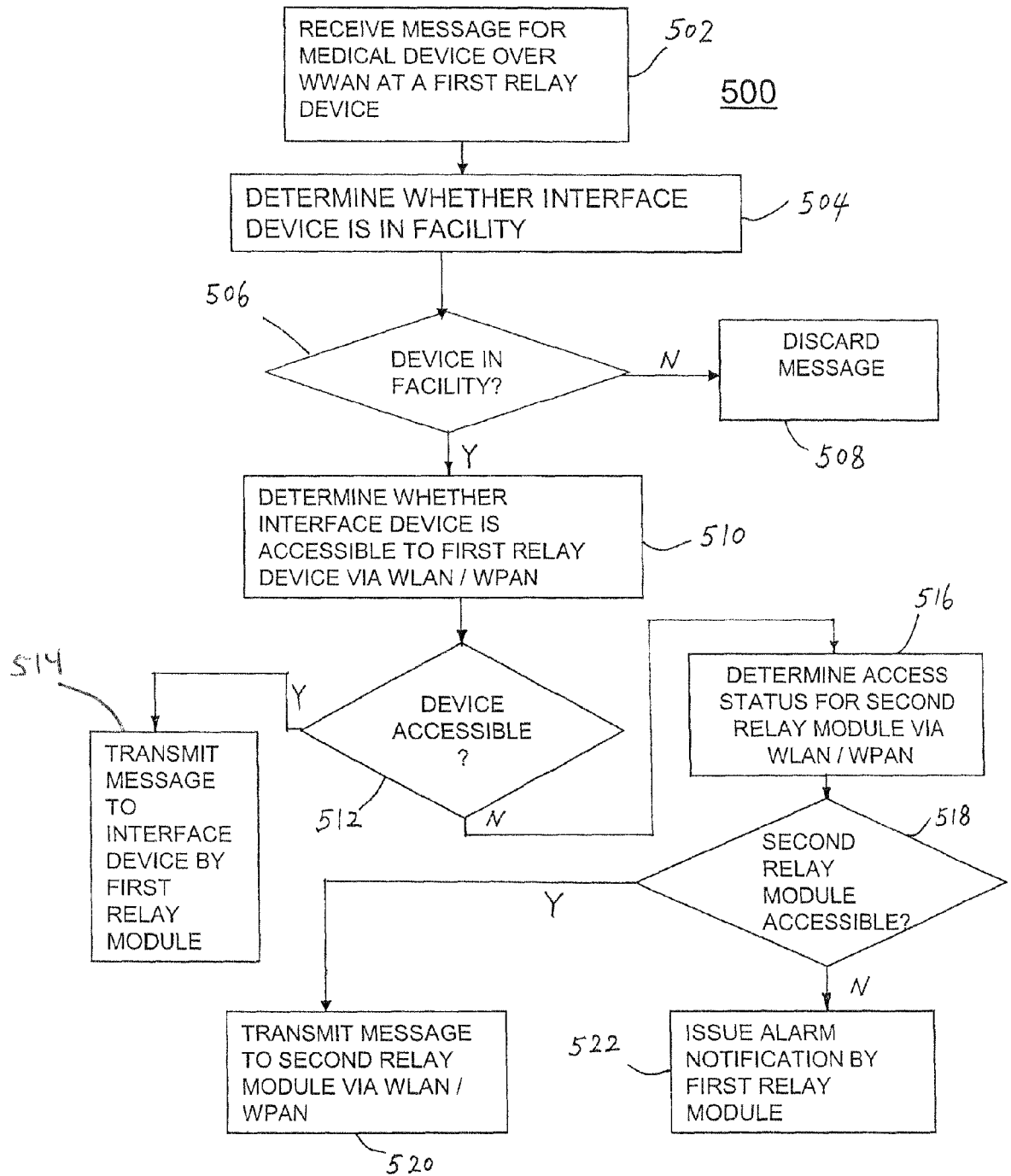
FIG. 5 presents a flow diagram illustrating a second exemplary method of operation for the relay module of FIG. 3(a)

FIG. 5 presents a flow diagram 500 illustrating another exemplary method of operation 500 for the architecture according to FIG. 1, relating to the transmission of a message from the access point 40 to be received by one of the medical devices 10. This enables the access point 40, for example, to communicate with medical devices in order to download new firmware or software, to respond to error messages initiated by the medical devices (for example, to re-set a device or remove it from service, or to run device diagnostics), and to operate the medical device (for example, to adjust a flow rate on a feeding pump).

At step 502 of the method 500, the message is received at the first one of the relay modules 30a from the access point 40 via a WWAN. At step 504, the one relay module 30 determines whether the message is intended to reach one of the interface circuits 15 and/or other relay modules 30, 30a located in the facility 20. This may be accomplished, for example, by maintaining a list of active devices 15 and modules 30, 30a in the buffer 35 or in a manner otherwise accessible to the one relay module 30a, or coding an identifier of the device 15 or module 30, 30a to include an identity of the facility 20 that is stored in the buffer 35 or is otherwise identifiable to the one relay module 30.

If the one relay module 30a determines at step 506 that the device 15 or module 30, 30a is not located in the facility, the one relay module 30 may preferably proceed to discard the message at step 508, and/or alternatively alert the access point 40 with a non-delivery message. If the interface device 15 is located in the facility 20, the one relay module 30a determines at step 510 whether the device 15 or relay module 30, 30a accessible to the one relay device 30a via the WLAN or WPAN (for example, by consulting a list stored in the buffer 35 or that is otherwise accessible to the one relay module 30a, or by instructing the transceiver 31 to send a handshake transmission directed to the interface device 15a, 15b and to listen for a reply).

If the one relay module 30a determines at step 512 that the device 15 or relay module 30, 30a is accessible, then at step 514, it transmits the message via network 16 to that device 15 or relay module 30, 30a via the transceiver 31. In this case, the message may again be broadcasted to all devices 15 and modules 30, 30a in communication with the one relay module 30a, and each device 15 or module 30, 30a may decide to act on or ignore the message (for example, by matching to an associated device ID or other identifier in the message). If the one relay module 30a alternatively determines at step 512 that the device or relay module is not accessible, then it proceeds at step 516 to determine whether a second relay module 30, 30a is accessible via the WLAN or WPAN (for example, by instructing the transceiver 31 to send a handshake transmission directed to the second relay module and to listen for a reply). If the second relay module 30, 30a is available, then the one relay module 30 forwards the message to the transceiver 31 for transmission to the second relay module 30, 30a over the WLAN or WPAN. If the second relay module 30, 30a is inaccessible, then this portion of the process 500 may preferably be repeated to search for a third relay module 30, 30a that is accessible. Alternatively, or in the event that no other relay module 30, 30a is available, the one relay module 30 may preferably issue an alarm notification at step 522, preferably in one of the same manners described above in reference to the method 400 of FIG. 4.

As illustrated for example in FIG. 2, each rely module 30, 30a is capable of communicating with a number of medical devices 10 over a period of time. It is possible that communications with some of the medical devices 10 are more time-critical with regard to patient safety than other. For example, consider communications with medical devices 10 including each of a thermometer, a feeding pump and a ventilator. In this case, communications with the ventilator would likely be most time-critical among the three medical devices, while communications with the thermometer might be least critical among the three medical devices.

In accordance with IEEE 802.14.15, if the network 16 is a ZIGBEE mesh network then there is little risk that communications from more than one medical device will contend for simultaneous access to the network 16. The network 16 operates with a protocol in which a transmitting device checks for energy on a wireless bus component of the network 16. If the bus is in use, the transmitting device waits a preselected amount of time before checking again, and only proceeds to transfer data when the energy level suggests that no other transmission is actively underway on the wireless bus. Nevetheless, for circumstances in which data packets transmitted by the medical devices 10 arrive at a relay module 30, 30a at nearly at the same time, there may be a need to manage an order of delivery by the relay module 30.

For example, consider a data packet from a ventilator indicating disconnection from a comatose patient, with possible fatality. In this case, the ventilator should be assigned priority for transmitting to one or more of remote monitoring devices 61, 62 and 63, while data transmissions from thermometer and pump are discontinued until a response to the data packet transmitted by the ventilator is received from one of the remote monitoring devices 61, 62 and 63. For example, the ventilator might be assigned a priority of 1, while the feeding pump is assigned a priority of 2 and the thermometer is assigned a priority of 3. The assigned priority is preferably indicated in each data packet transmitted by and to the medical devices, for example, as a "priority nibble."

With reference to FIG. 3(a), the processor 34 may be configured to read the priority nibble from each received data packet, and to instruct the data processing circuit 33 to place the data packet at a logical position in the buffer element 35 based upon the priority designation. For example, critical data packets for the ventilator would be positioned for first retrieval and transmission by the relay module 30, 30a, and other data packets are positioned in order according to their priority.

In addition, under circumstances where urgent commands may need to be transmitted by one of the remote monitoring devices 61, 62 and 63 anticipated based on an urgent data packet from the ventilator, the wireless relay module 30, 30a may in addition discontinue reception of any new medical device information from other medical devices until the urgent commands are relayed and an associated alarm condition has been terminated or released.

The novel wireless relay module disclosed herein for providing networked communications between a series of medical devices and a remote monitoring device provides a number of distinct advantages in comparison to other monitoring systems. By employing wireless relay networks such as ZIGBEE networks based on the IEEE 802.15.4 standard, for wireless communications between the medical devices 10 and relay modules 30, 30a in accordance with one embodiment of the invention, power and size requirements can be minimized so that the interface circuits 15 can be easily and inexpensively applied to and/or integrated with the medical devices 10.

By introducing relay modules 30a that are part of the wireless relay networks and are directly able to access off-site monitoring devices via a WWAN, access to and reliance on existing and potentially unreliable LAN facilities at a facility can be avoided. By incorporating relay features into the relay modules 30a that relay communications from a first relay module 30a to a second relay module 30a in the event that WWAN access to the first relay module 30a has been compromised, the present invention improves reliability and enables the use of conventional, low-cost cellular transceivers in the relay modules 30a for accessing the WWAN.

Figure 6:
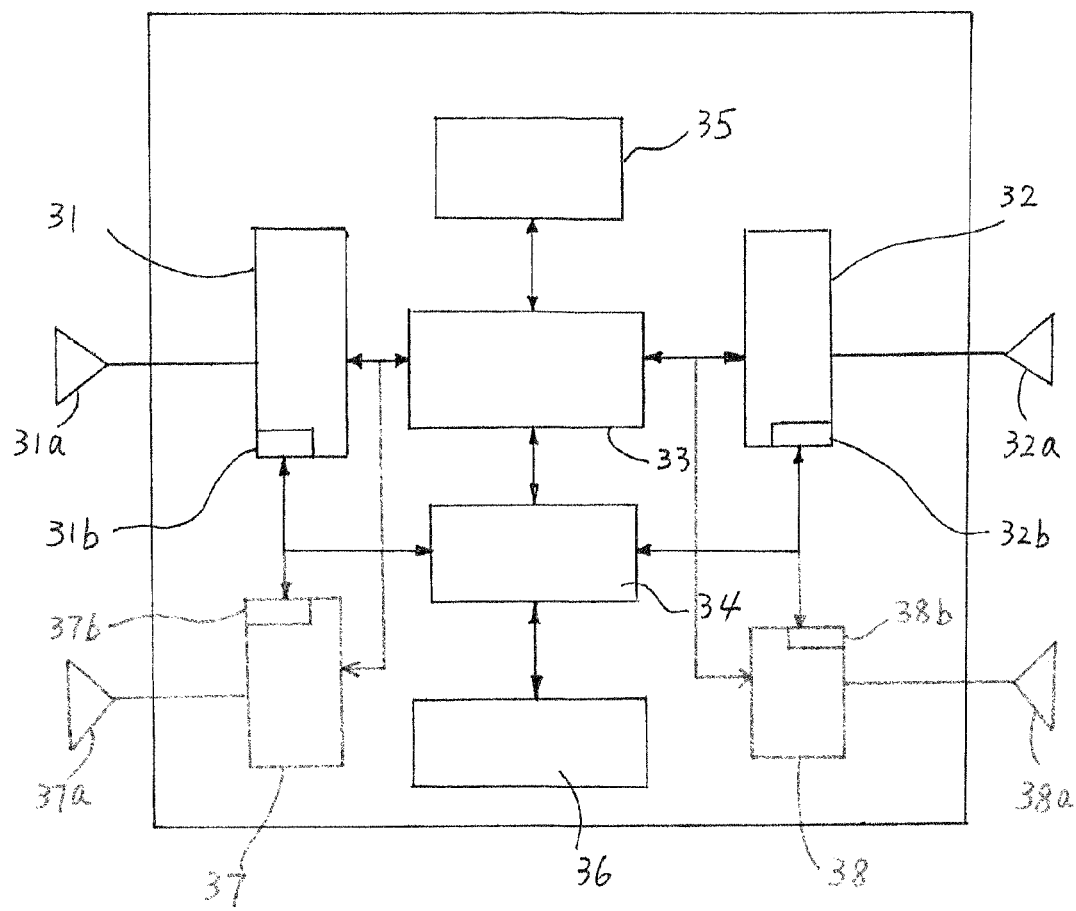
FIG. 6 presents a schematic diagram illustrating an alternative exemplary wireless relay module to that depicted in FIG. 3(a) according to the present invention.

FIG. 6 depicts a block diagram illustrating exemplary components of an alternative configuration for the relay module 30a to the configuration of relay module 30a depicted in FIG. 3(a). Identical reference numbers in FIGS. 3(a) and (6) refer to identical components, for example, transceivers 31 and 32, data processing circuit 33 and processor 34. In FIG. 6, as in FIG. 3(a), the relay module 30a includes transceiver 31 for wirelessly communicating with interface circuits 15 (shown in FIGS. 1 and 2) and other relay modules 30, 30a in a particular WLAN or WPAN network 16 (shown in FIG. 2) via antenna 31a. Also, in FIG. 6, as in FIG. 3(a), the relay module 30a further includes a transceiver 32 for wirelessly communicating with the access point 40 over a particular WWAN (shown in FIG. 2) via an antenna 32a.

Added components to the relay module 30a in FIG. 6 not present in FIG. 3(a) include an additional transceiver 37, similar to transceiver 31, for wirelessly communicating via antenna 37a with interface circuits and other relay modules capable of communicating over a different WLAN or WPAN network than the network used by transceiver 31. Correspondingly, the relay module 30a in FIG. 6 includes yet a further transceiver 38, similar to transceiver 32, for wirelessly communicating via antenna 38a with an access point over a different WWAN than the WWAN used by transceiver 32.

Each of the transceivers 31, 32, 37 and 38 is in communication with data processing circuit 33, which is configured to operate under the control of processor 34 to accept data received by the transceivers 31, 32, 37 and 38 and store the received data in buffer element 35. In addition, the data processing circuit 33 is further configured to retrieve data from buffer element 35 under the direction of processor 34 and provide the retrieved data to a selected one of the transceivers 31, 32, 37 or 38 for transmission. In order to make a selection, the processor 34 is configured to communicate with respective status modules 31b, 32b, 37b and 38b of respective transceivers 31, 32, 37 or 38 in order to determine a communications status of the transceivers 31, 32, 37 or 38. It should be understood that the data processing circuit 3 and processor 34 may be implemented as separate integrated circuits or chip sets or their functions may be combined and implemented on single integrated circuits or chip set The processor 34 is also preferably in communication with an input/output circuit 36, which provides signals to one or more display elements of the relay module 30a, for example, for indicating a start-up or current status of the relay module 30a, including communication or connection status with the WLAN or WPAN networks and WWANs networks. Input/output circuit 36 may also be configured to provide signals to indicate an A/C power loss, and or to be responsive to signals provided by one or more input devices provided in proximity to the one or more display elements.

Figure 3E:
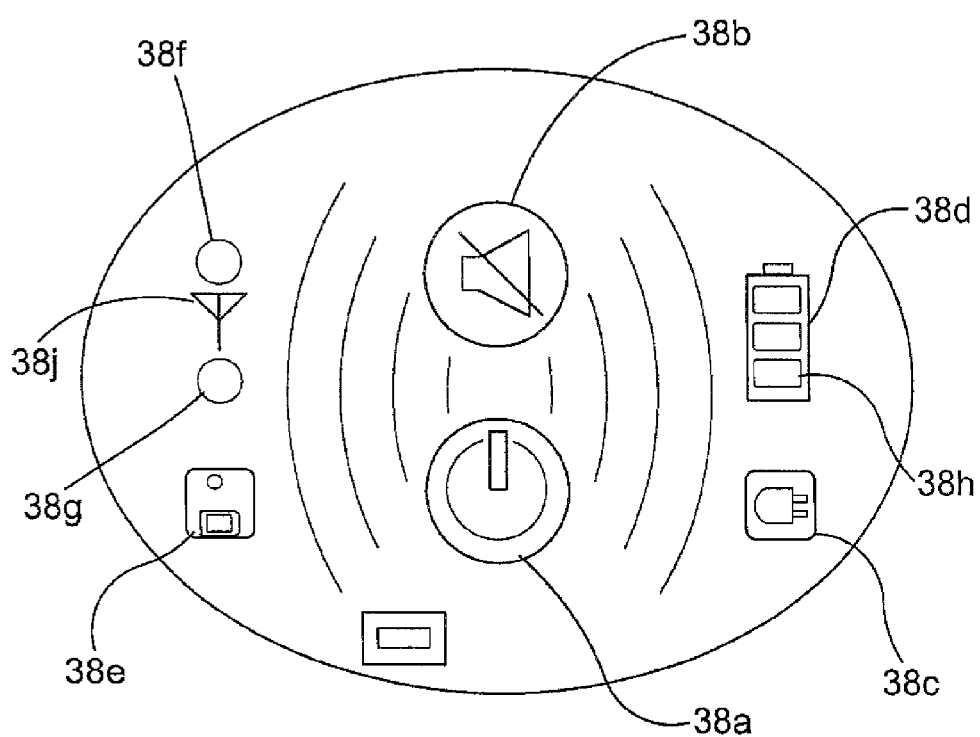

A control panel useable for the module 30a of FIG. 6 may be substantially similar to the control panel 38 depicted in FIG. 3(e) with corresponding multiple indicators 38e for indicating the status of the different WLAN or WPAN networks, and/or multiple indicators 38f for indicating the status of the different WWANs.

Figure 7:
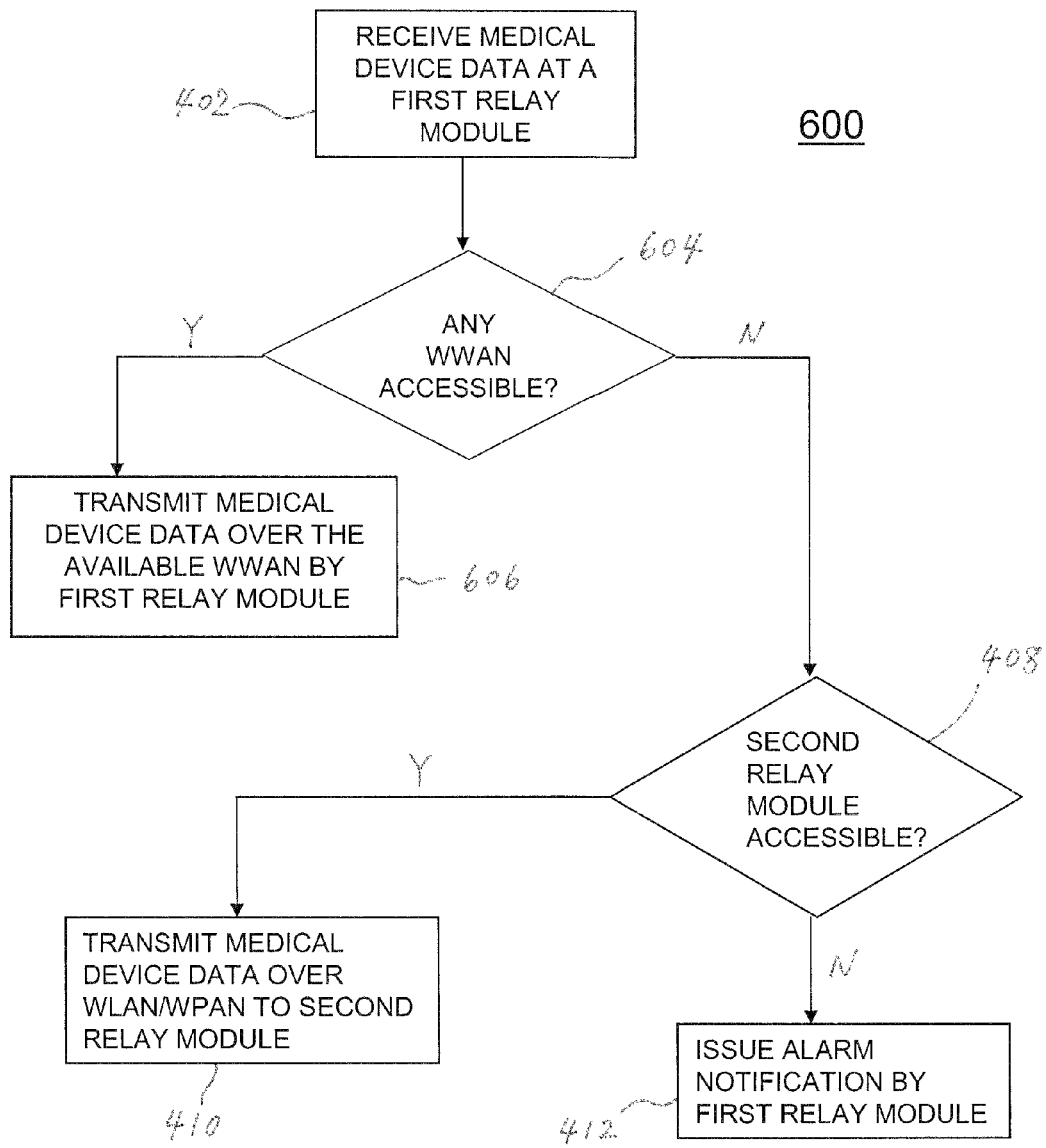
FIG. 7 presents a flow diagram illustrating an exemplary method of operation for the relay module of FIG. 6.

The relay module 30a configuration of FIG. 6 may be operated in a substantially similar manner to the relay module 30a configuration of FIG. 3a employing, for example, corresponding methods of operation to those depicted in FIGS. 4 and 5 incorporating the use of a plurality of WWANs or WLAN or WPAN networks. However, in performing methods of operation for the relay module 30a of FIG. 6, the depicted steps in FIGS. 4 and 5 may be employed with the further transceiver selections of the additional transceivers 37 and 38. For example, FIG. 7 depicts a method of operation 600 for the relay module 30a configuration of FIG. 6 that is analogous to the method 400 of FIG. 4 for the relay module 30a configuration of FIG. 3(a). Methods 400 and 600 include substantially identical steps except method 600 substitutes steps 604 and 606 for steps 404 and 406 of method 400. These substituted steps 604 and 606 are similar to the corresponding steps 404 and 406 expanded to utilize the additional transceivers 37 and 38 of FIG. 6.

Referring to FIG. 7, after medical device data is received over a WLAN or PLAN network by transceivers 31 or 37 of FIG. 6 in step 402, the relay module 30a determines if any WWAN is accessible by transceivers 32 or 38. If no WWAN is accessible the method 600 then continues to step 408 and performs substantially the same operations as described with respect to steps 408, 410 and 412 in FIG. 4. Otherwise, if a WWAN is determined accessible in step 604 of FIG. 7, the method 600 proceeds to step 606. In step 606, the method 600 transmits the medical data over the available WWAN via transceiver 32 or 38 to the appropriate access point.

Moreover, to the extent to that in step 604 of FIG. 7 there are more than one WWAN accessible then in step 606 the controller 33 in FIG. 6 must determine which one of the accessible WWANs the medical data should be transmitted over by either of transceivers 32 or 38. Such determination can be made by many different criteria or rules including, for example, based upon signal strength, cost, time of day, day of week or preferences of a network manager or other user.

It is possible to limit the configuration of cellular transceivers to just the relay modules 30a in a facility, instead of modules 30 and 30a. In addition, by providing the relay modules 30a in a compact enclosure, the relay modules 30a are easily connected to reliable commercial power sources and easily moved when needed to reconfigure the wireless relay networks according to facilities changes. The portability for ambulatory use that is provided by battery back-up is an additional advantage.

It should of course, be understood that while the present invention has been described with respect to disclosed embodiments, numerous variations are possible without departing from the spirit and scope of the present invention as defined in the claims. For example, the present invention may be based on any of a number of current and future WPAN, WLAN and WWAN standards beyond those explicitly described herein. It should also be understood that it is possible to use exclusively relay modules 30a in the WLAN or WPAN network 16 of FIGS. 1 and 2, with transceivers for communicating with other relay modules as well as over the WWAN.

In addition, respective interface circuits useable with the present invention may include components of and perform the functions of the module 30 to provide greater flexibility in accordance with the present invention. Further, numerous configurations of components for relay module 30a are useable with the present invention beyond the components shown in FIG. 3. For instance, an input-output buffer may be used with respective switches under control of a processor for directing medical device data to transceivers 31, 32, 37 or 38 as needed. Moreover, it is intended that the scope of the present invention include all other foreseeable equivalents to the elements and structures as described herein and with reference to the drawing figures. Accordingly, the invention is to be limited only by the scope of the claims and their equivalents.

We claim:

1. A wireless relay module comprising:
a first receiver capable of wirelessly receiving medical device data over a first wireless relay network from at least one medical device, wherein the at least one medical device is coupled to an interface circuit which is configured for communicating with at least one of a plurality of wireless relay modules via at least one of a plurality of wireless relay networks;
a first transmitter capable of wirelessly transmitting data over a first internet-accessible wireless communications network;
a second transmitter capable of wirelessly transmitting data over a second, different internet-accessible wireless communications network;
a third transmitter capable of wirelessly transmitting medical device data to a second wireless relay module over the first wireless relay network; and
a processor coupled to said first, second, and third transmitters of the wireless relay module, wherein said processor is capable of determining a device status for each of the at least one medical devices and a connection status of each of said first, second, and third transmitters of the wireless relay module; and
a status module in communication with said processor, wherein said status module is capable of determining an access status of the first wireless relay network, the first internet-accessible wireless communications network, the second internet-accessible wireless communications network and providing the access status to said processor for selecting the first, second, or third transmitter for medical device data transmission based upon at least two of: (1) the access status of the first wireless relay network, the first internet-accessible wireless communications network, the second internet-accessible wireless communications network determined by the status module; (2) the device status for each of the at least one medical devices determined by the processor; and (3) the connection status of said first, second, and third transmitters of the wireless relay module determined by the processor wherein said first transmitter is configured to securely transmit data over a first internet-accessible wireless communications network;
said second transmitter is configured to securely transmit data over a second, different internet-accessible wireless communications network; and
said third transmitter is configured to securely transmit medical device data to a second wireless relay module over the first wireless relay network.

2. The wireless relay module of claim 1, wherein said third transmitter is further capable of transmitting operating instructions to said at least one medical device.

3. The wireless relay module of claim 2, further comprising: a second receiver capable of wirelessly receiving said operating instructions from at least one of said first or second internet-accessible wireless communications networks; and a memory electrically connected to said processor, said memory capable of buffering said received operating instructions destined for respective ones of said medical devices, wherein said processor controls the order and/or priority for transmission of said operating instructions to said respective ones of said medical devices.

4. The wireless relay module of claim 3, wherein the second receiver is capable of wirelessly receiving said operating instructions from said first internet-accessible wireless communications network, further comprising: a third receiver capable of wirelessly receiving said operating instructions from said second internet-accessible wireless communications network.

5. The wireless relay module of claim 4, further comprising: a fourth transmitter capable of wirelessly transmitting medical device data; wherein said processor is further coupled to said first receiver, is capable of determining a type of the wireless relay network according to the medical device data received from the at least one medical device, and is further capable of selecting one of the third transmitter or the fourth transmitter according to the type of the wireless relay network for transmitting operating instructions to the at least one medical device.

6. The wireless relay module of claim 1, further comprising: a wireless communications network indicator on communication with said status module for providing a status indication of a determined status of potential communications over at least one of said first or second wireless communications networks by said wireless relay module.

7. The wireless relay module of claim 1, further comprising: a wireless relay network indicator electrically connected to said processor for providing a status indication of a determined status of potential communications over said wireless relay network.

8. The wireless relay module of claim 1 wherein said wireless relay network is a mesh network.

9. The wireless relay module of claim 1 wherein said wireless relay network is a relay-enable Bluetooth network.

10. The wireless relay module of claim 1, wherein one of said first or second internet-accessible wireless communications networks is a mobile communications network.

11. The wireless relay module of claim 10 wherein one or more of said first or second mobile communications networks is a CDMA-based, GSM-based or WiMax-based network.

12. The wireless relay module of claim 10, wherein the second internet-accessible wireless communications networks is selected from the group consisting of metropolitan area networks (MANs), campus area Networks (CANs), local area networks (LANs), home area networks (HANs), personal area networks (PANs) and body area networks (BANs).

13. The wireless relay module of claim 1 wherein said first, second and third transmitters are configured to securely transmit encrypted medical device data.

14. The wireless relay module of claim 1 further comprising: a second receiver coupled to the processor and capable of wirelessly receiving medical device data over a second wireless relay network; and a fourth transmitter coupled to the processor and capable of wirelessly transmitting medical device data to a second wireless relay module over the second wireless relay network.

15. A process for operating a relay module in a medical device wireless network, comprising:
receiving data from at least one medical device over a wireless relay network, each of the at least one medical devices coupled to an interface circuit which is configured for communicating with one of a plurality of wireless relay modules via one of a plurality of wireless relay networks;
determining an access status of first and second internet-accessible wireless communications networks in respective communication with a first transmitter and a second transmitter of said relay module;
determining an access status of the first wireless relay network in respective communication with a third transmitter of said relay module;
determining a device status for each of the at least one medical devices;
determining a connection status of the first, second, and third transmitters of the relay module;
in response to the determined access status of the first or second internet-accessible wireless communications network, device status for each of the at least one medical devices, and the connection status of the first and second transmitters of the relay module and the first or second internet-accessible wireless communications network satisfying a particular criteria, transmitting said data from said at least one medical device over said first or second internet-accessible wireless communications network by said first or second transmitter; and
in response to the determined access status of the first or second internet-accessible wireless communications network, device status for each of the at least one medical devices, and connection status of the first and second transmitters of the relay module and the first or second internet-accessible wireless communications network failing to satisfy the particular criteria, and the access status of the first wireless relay network satisfying a particular criteria, transmitting said data from said at least one medical devices by a third transmitter in communication with the wireless relay network to a second relay module over the wireless relay network wherein:
said first transmitter is configured to securely transmit data over a first internet-accessible wireless communications network;
said second transmitter is configured to securely transmit data over a second, different internet-accessible wireless communications network; and
said third transmitter is configured to securely transmit medical device data to a second wireless relay module over the first wireless relay network.

16. The process of claim 15 further comprising:
receiving operating instructions over the first or second internet-accessible wireless communications network intended for said at least one medical devices; and
transmitting said received operating instructions to said intended ones of said at least one medical device.

17. The process of claim 15 further comprising:
buffering said received operating instructions destined for respective ones of said medical devices; and
controlling at least one of an order or priority for transmission of said operating instructions to said respective ones of said medical devices.

18. The process of claim 15, wherein said wireless relay network is a ZIGBEE network.

19. The process of claim 15, wherein said wireless relay network is a relay enabled Bluetooth network.

20. The process of claim 15, wherein at least one of said first or second wireless communications networks is a communications channel of a mobile communications network.

21. The process of claim 20, wherein said mobile communications network is a CDMA, GSM or WiMax-based network.

22. The process of claim 15, wherein the determining further comprises measuring a state of each of said first and second wireless communications networks; and determining said status of said first and second wireless communications networks as a function of said measured states of said first and second wireless communications networks.

23. The process of claim 22, wherein the measured state is related to a signal strength of the measured wireless communication network.

24. The process of claim 22, wherein the measured state is related to a latency of communications in the measured wireless communication network.

25. The process of claim 15, wherein the particular criteria includes the identification of a user selection of one of the first or second wireless communications networks.

26. The process of claim 15, wherein the said status is determined as a function of a value of a data element stored by a storage element of said relay module.

27. The wireless relay module of claim 1, wherein the second internet-accessible wireless communications network is different from the first internet-accessible wireless communications network.

28. The wireless relay module of claim 1, wherein the access status is indicative of access for the transceiver to a wireless wide-area networks (WWAN).

29. The process of claim 15 further comprising issuing an alarm notification if the access status of the first wireless relay network fails to satisfy the particular criteria.

* * * * *